United States Patent
Moretti et al.

(10) Patent No.: US 12,178,392 B2
(45) Date of Patent: Dec. 31, 2024

(54) INTERCHANGEABLE IMAGING MODULES FOR A MEDICAL DIAGNOSTICS DEVICE WITH INTEGRATED ARTIFICIAL INTELLIGENCE CAPABILITIES

(71) Applicant: AI Optics Inc., New York, NY (US)

(72) Inventors: Luke Michael Moretti, New York, NY (US); Andrew DiGiore, New York, NY (US)

(73) Assignee: AI Optics Inc., New York, NY (US)

( * ) Notice: Subject to any disclaimer, the term of this patent is extended or adjusted under 35 U.S.C. 154(b) by 409 days.

(21) Appl. No.: 17/678,903

(22) Filed: Feb. 23, 2022

(65) Prior Publication Data

US 2022/0280028 A1     Sep. 8, 2022

Related U.S. Application Data (60) Provisional application No. 63/156,237, filed on Mar. 3, 2021.

(51) Int. Cl.
*A61B 1/00* (2006.01)
*A61B 1/227* (2006.01)
(Continued)

(52) U.S. Cl.
CPC ...... *A61B 1/00105* (2013.01); *A61B 1/00039* (2013.01); *A61B 1/00103* (2013.01);
(Continued)

(58) Field of Classification Search
CPC ............ A61B 1/00105; A61B 1/00039; A61B 1/00103; A61B 1/227; A61B 1/32;
(Continued)

(56) References Cited

U.S. PATENT DOCUMENTS 5,912,720 A     6/1999  Berger
8,687,862 B2    4/2014  Hsu
(Continued)

FOREIGN PATENT DOCUMENTS

JP    2020178903      11/2020
KR    20190091857     8/2019
(Continued)

OTHER PUBLICATIONS

Center for Innovation (L V Prasad Eye Institute), Open Indirect Ophthalmoscope, https://lvpmitra.com/oio#introduction (2021).
(Continued)

*Primary Examiner* — Mohammed A Hasan
(74) *Attorney, Agent, or Firm* — Knobbe Martens Olson & Bear LLP (57) ABSTRACT

A medical diagnostic instrument can include a housing with a mounting interface configured to support a plurality of imaging devices, each of the plurality of imaging devices configured to capture image data of a different anatomical region of a patient. The instrument can include an electronic processing circuitry, which can include a memory and a processor. The processor can be configured to, responsive to an attachment of an imaging device of the plurality of imaging devices to the mounting interface, retrieve from the memory and execute at least one machine learning model from a plurality of machine learning models configured to identify, based on image data, one or more diseases of the patient. The at least one machine learning model can be configured to identify one or more diseases of an anatomical region of the patient an image data of which the imaging device is configured to capture.

20 Claims, 4 Drawing Sheets

(51) Int. Cl.
*A61B 1/32* (2006.01)
*A61B 3/00* (2006.01)
*A61B 3/14* (2006.01)
*A61B 90/94* (2016.01)
*A61B 90/98* (2016.01)

(52) U.S. Cl.
CPC ............... *A61B 1/227* (2013.01); *A61B 1/32* (2013.01); *A61B 3/0041* (2013.01); *A61B 3/14* (2013.01); *A61B 90/94* (2016.02); *A61B 90/98* (2016.02)

(58) Field of Classification Search
CPC ......... A61B 3/0041; A61B 3/14; A61B 90/94; A61B 90/98; A61B 1/000096; A61B 1/00059; A61B 3/12
USPC ............................................................ 351/206
See application file for complete search history.

(56) References Cited

U.S. PATENT DOCUMENTS

| | | | |
|---|---|---|---|
| 8,960,910 | B2 | 2/2015 | Alasaarela |
| 9,033,507 | B2 | 5/2015 | Alasaarela |
| 9,757,031 | B2 | 9/2017 | Wang |
| 10,376,142 | B2 | 8/2019 | Dirghangi |
| 11,457,983 | B1 * | 10/2022 | Roh ............... A61B 34/25 |
| 11,510,733 | B1 * | 11/2022 | Roh ............... A61B 34/10 |
| 2005/0234300 | A1 | 10/2005 | Farrell |
| 2011/0299036 | A1 | 12/2011 | Goldenholz |
| 2012/0257163 | A1 | 10/2012 | Dyer |
| 2018/0055357 | A1 | 3/2018 | Meyerson |
| 2018/0153399 | A1 | 6/2018 | Fink |
| 2019/0133435 | A1 | 5/2019 | Browne |
| 2019/0216308 | A1 | 7/2019 | Senaras et al. |
| 2020/0170564 | A1 | 6/2020 | Jiang |
| 2020/0196869 | A1 | 6/2020 | Narayanan |
| 2020/0405148 | A1 | 12/2020 | Tran |
| 2021/0035301 | A1 | 2/2021 | Soares |

FOREIGN PATENT DOCUMENTS

| | | |
|---|---|---|
| KR | 102032193 | 10/2019 |
| KR | 20190129247 | 11/2019 |
| WO | WO 2016/179370 | 11/2016 |
| WO | WO 2017/031099 | 2/2017 |
| WO | WO 2020/173516 | 9/2020 |

OTHER PUBLICATIONS

Bleicher, Ariel, Teenage Whiz Kid Invents an AI System to Gianose her Grandfather's Eye Disease, IEEE Spectrum (2017). https://spectrum.IEEE.org/the-human-os/biomedical/diagnostics/teenage-whiz- kid-invents-an-ai-system-to-diagnose-her-grandfathers-eye-disease.

Masumoto, et al, Deep-learning classifier with an ultrawide-field scanning laser ophthalmoscope detects glaucoma visual field severity, Glaucoma Journal 27(7):647-652 (2018).

Ting, et al., Artificial intelligence and deep learning in ophthalmology, Br J. Ophthalmol 103:167-175 (2019).

WelchAllyn Standard Ophthalmoscope (https://www.welchallyn.com/en/products/categories/physical- exam/eye-exam/ophthalmoscopes--traditional-direct/35v_standard_ophthalmoscope.html# ) 2018.

WelchAllyn PanOptic Brochure (2016).

WelchAllyn iExaminer (https://www.welchallyn.com/en/microsites/iexaminer.html) 2018.

D-Eye Smartphone-Based Retinal Imaging System (https://www.d-eyecare.com/en_US/product#features) (retrieved in Mar. 2021).

Horus 100 fundus camera (http://www.miis.com.tw/product01.php?no=36) 2014.

Horus 200 portable fundus camera (http://www.miis.com.tw/product01.php?no=84) 2014.

Microclear Luna Fundus Camera (https://www.microcleartech.com/en/productInfo?p=hfc_v2) (retrieved in Mar. 2021).

Mediworks FC 161 hand-held fundus camera (https://www.mediworks.biz/en/product/handheld-fundus- camera-fc161).

Remidio NMFOP (https://www.remidio.com/fop.php) (retrieved in Mar. 2021).

Welch Allyn RetinaVue 700 Imager (2019).

IDx-DR Autonomous AI (https://dxs.ai/products/dermatology/autonomous-ai/) 2020.

IDx-DR Overview: Close Care Gaps, Prevent Blindness (https://dxs.ai/products/idx-dr/idx-dr-overview/) 2020.

EyeNuk EyeArt screening system (https://www.eyenuk.com/en/) (retrieved in Mar. 2021).

Optomed Aurora User Manual (2019).

Volk Pictor Prestige User Manual (2019).

* cited by examiner

INTERCHANGEABLE IMAGING MODULES FOR A MEDICAL DIAGNOSTICS DEVICE WITH INTEGRATED ARTIFICIAL INTELLIGENCE CAPABILITIES

CROSS-REFERENCE TO RELATED APPLICATIONS

This application claims priority to U.S. Provisional Application No. 63/156,237 filed on Mar. 3, 2021, which is incorporated by reference in its entirety.

TECHNICAL FIELD

Disclosed are systems and methods that can perform analysis of a body part with medical diagnostics devices, for example, using artificial intelligence (AI) having a modular architecture.

BACKGROUND

Diagnostic devices provide clinicians with the ability to screen for various diseases. For example, a fundus (or retina) camera is an instrument for inspecting the retina of the eye. Many ophthalmologic, neurologic, and systemic diseases can cause structural abnormalities in the retina, which alter the visual appearance of the retina. These structural and visible abnormalities are known as biomarkers, and they may indicate the presence of a disease. For example, diabetics have high levels of circulating blood sugar that, over time, can cause damage to the small vessels in the retina and lead to the formation of microaneurysms. Such microaneurysms indicate the presence of diabetic retinopathy, which is a diabetes complication that affects eyes, caused by damage to the blood vessels of the light-sensitive tissue at the retina. Clinicians use fundus cameras to visualize and assess a patient's retina for biomarkers in order to diagnose the disease. As another example, an otoscope can be used to examine the ear for abnormalities. As yet another example, a dermatology scope can be used for examining the skin for abnormalities. The multitude of different diagnostic devices can be cumbersome to use and expensive to procure and maintain in good working condition.

SUMMARY

In some implementations, a medical diagnostic instrument can include a housing with a mounting interface configured to support a plurality of imaging devices. Each of the plurality of imaging devices can be configured to capture image data of a different anatomical region of a patient. The instrument can include an electronic processing circuitry supported by the housing. The electronic processing circuitry can include a memory and a processor. The processor can be configured to, responsive to an attachment of an imaging device of the plurality of imaging devices to the mounting interface, retrieve from the memory and execute at least one machine learning model from a plurality of machine learning models configured to identify, based on image data, one or more diseases of the patient. The at least one machine learning model can be configured to identify one or more diseases of an anatomical region of the patient an image data of which the imaging device is configured to capture.

The diagnostic instrument of the preceding paragraph or any of the diagnostic instruments disclosed herein can include one or more of the following features. The mounting interface can include a connection configured to provide at least one of power or illumination to an imaging device attached to the mounting interface. The housing can include an image sensor configured to capture image data. The plurality of imaging devices may not include any image sensors. The processor can be configured to, responsive to the attachment of the imaging device, determine an identification of the imaging device based on at least one of: retrieving the identification from a memory of the imaging device, receiving the identification via radio frequency identification (RFID) or near field communication (NFC), determining the identification from a visual marker positioned on the imaging device, or determining the identification from the image data. The visual marker can be a quick response (QR) code.

The diagnostic instrument of any of the preceding paragraphs or any of the diagnostic instruments disclosed herein can include one or more of the following features. The processor can be configured to detect the attachment of the imaging device based on receiving an electrical signal generated by the attachment of the imaging device. The housing can include a user interface at least partially supported on an exterior of the housing. The processor can be configured to configure the user interface responsive to the attachment of the imaging device. The user interface can be a display. The mounting interface can be configured to facilitate at least one of a mechanical or magnetic attachment of the imaging device.

The diagnostic instrument of any of the preceding paragraphs or any of the diagnostic instruments disclosed herein can include one or more of the following features. Different anatomical regions of the patient can include an eye, ear, or skin of the patient. The anatomical region of the patient can be an eye of the patient, and the imaging device can include a cup positioned at a distal end of the imaging device. The cup can be configured to be an interface between instrument and the eye. The cup can be disposable. The anatomical region of the patient can be an ear of the patient, and the imaging device can include an ear specula positioned at a distal end of the imaging device. The ear specula can be configured to be an interface between instrument and the ear. The ear specula can be disposable. The housing can be portable. The housing can include a body and a handle. The handle can be connected to the body and configured to be held by a user.

A method of operating the instrument of any of the preceding paragraphs or any of the instruments disclosed herein is provided.

BRIEF DESCRIPTION OF DRAWINGS

Throughout the drawings, reference numbers may be re-used to indicate correspondence between referenced elements. The drawings are provided to illustrate example embodiments described herein and are not intended to limit the scope of the disclosure.

DETAILED DESCRIPTION

Introduction

Many optical-based diagnostic devices (sometimes referred to as imaging devices) share common components and have similar features. For example, retina cameras, otoscopes, and dermatology scopes include optics, illumination, processing modules, and user interfaces. Portable imaging devices typically include a single fixed optical system that cannot be swapped for different imaging applications or anatomies (for instance, imaging the eye, ear, or skin). Moreover, when artificial intelligence (AI) image analysis is incorporated (or embedded) into the imaging device, different AI models or algorithms may be needed for different imaging applications or anatomies. When imaging different anatomy (such as, retina, ear, or skin), the set of possible diseases that may be present also changes. For example, a retina camera can utilize one or more AI models to detect diabetic retinopathy, glaucoma, cataract, or other eye abnormalities. As another example, an otoscope can utilize one or more AI models to detect wax obstruction, chronic perforations, acute otitis media, ear infection, or other ear abnormalities. As yet another example, a dermatology scope can utilize one or more AI models to detect lesions, moles, melanomas, or other skin abnormalities.

Unlike a clinician who has the benefit of the context of the clinical environment and the knowledge of which body part is being evaluated, an AI system would only have the image itself to make a disease determination. In addition, AI models are generally trained to look for conditions or diseases related to the specific anatomy being imaged. Therefore, a portable imaging system that is capable of imaging different anatomies through the use of different optical and optomechanical attachments that can inform the embedded AI system of the particular anatomical region under evaluation can improve the disease detection by the embedded AI system and ultimately increase the utility and accuracy of the portable system.

Disclosed systems and methods generally relate to detecting diseases of different parts of the body (such as, the eye, ear, or skin). Different types of interchangeable imaging devices or modules can be supported by a base unit or system to facilitate imaging different parts of the body. By detecting attachment of a particular imaging device or module, the base system can determine the context for which body part is likely to be imaged. The base system can load the appropriate anatomy or disease specific AI (or machine learning) model(s) that perform the image analysis and disease detection. In some cases, the system can use an AI model specifically trained to identify the specific anatomy being imaged and, thus, alternatively or additionally, use the output of this AI model to inform the system of the particular anatomical region under evaluation and/or the attachment connected to the system. This can facilitate anatomy-specific image capture and analysis and increase the accuracy of disease detection. The combination of the base system and interchangeable imaging devices can be used for the diagnosis of various body parts and detection of various diseases. Providing clinicians with a diagnostic tool having a standardized base system and interchangeable imaging modules can make diagnosis less complex and easier to perform as well as reduce overall costs.

Medical Diagnostics Devices with On-Board AI

A device with integrated artificial intelligence (AI) can be used to assess a patient's body part to detect a disease. The device may be portable or handheld by a user (which may be a patient or a healthcare provider). For example, the device can be a retina camera configured to assess a patient's eye (or retina) and, by using an on-board AI retinal disease detection system, provide real-time analysis and diagnosis of disease that caused changes to the patient's retina. Easy and comfortable visualization of the patient's retina can be facilitated using such retina camera, which can be placed over the patient's eye, display the retina image on a high-resolution display, capture and store a retina image (for instance, by utilizing screenshot capabilities), analyze a captured image by the on-board AI system, and provide determination of presence of a disease.

Such retina camera can perform data collection, processing, and diagnostics tasks on-board without the need to connect to another computing device or to cloud computing services. This approach can avoid potential interruptions of the clinical workflow when using cloud-based solutions, which involve transfer of data over the network and, accordingly, rely on network connectivity. This approach can facilitate faster processing because the device can continually acquire and process images without needing intermediary upload/download steps, which may be slow. Such retina camera can potentially improve accuracy (for instance, as compared to retina cameras that rely on a human to perform analysis), facilitate usability (for example, because no connectivity is used to transfer data for analysis or transfer results of the analysis), provide diagnostic results in real-time, facilitate security and guard patient privacy (for example, because data is not transferred to another computing device), or the like. Such retina camera can be used in many settings, including places where network connectivity is unreliable or lacking.

Such retina camera can allow for better data capture and analysis, facilitate improvement of diagnostic sensitivity and specificity, and improve disease diagnosis in patients. Existing fundus cameras may lack one or more of portability, display, on-board AI capabilities, etc. or require one or more of network connectivity for sharing data, another device (such as, mobile phone or computing device) to view collected data, rigorous training of the user, etc. In contrast, allowing for high-quality retinal viewing and image capturing with faster analysis and detection of the presence of disease via on-board AI system and image-sharing capabilities, the retina cameras described herein can potentially provide improved functionality, utility, and security. Such retina camera can be used in hospitals, clinics, and/or at home. The retina cameras or other instruments described herein, however, need not include each of the features and advantages recited herein but may possibly include any individual one of these features and advantages or may alternatively include any combination thereof.

As another example, the device can be an otoscope configured to assess a patient's ear and, by using an on-board artificial intelligence (AI) ear disease detection system, possibly provide immediate analysis and/or diagnosis of diseases of the patient's ear. Such an otoscope can have one or more advantages described above or elsewhere in this disclosure. As yet another example, the device can be a dermatology scope configured to assess a patient's skin and, by using an on-board artificial intelligence (AI) skin disease detection system, possibly provide immediate analysis and/or diagnosis of diseases of the patient's skin. Such a dermatology scope can have one or more advantages described above or elsewhere in this disclosure.

Figure 1:
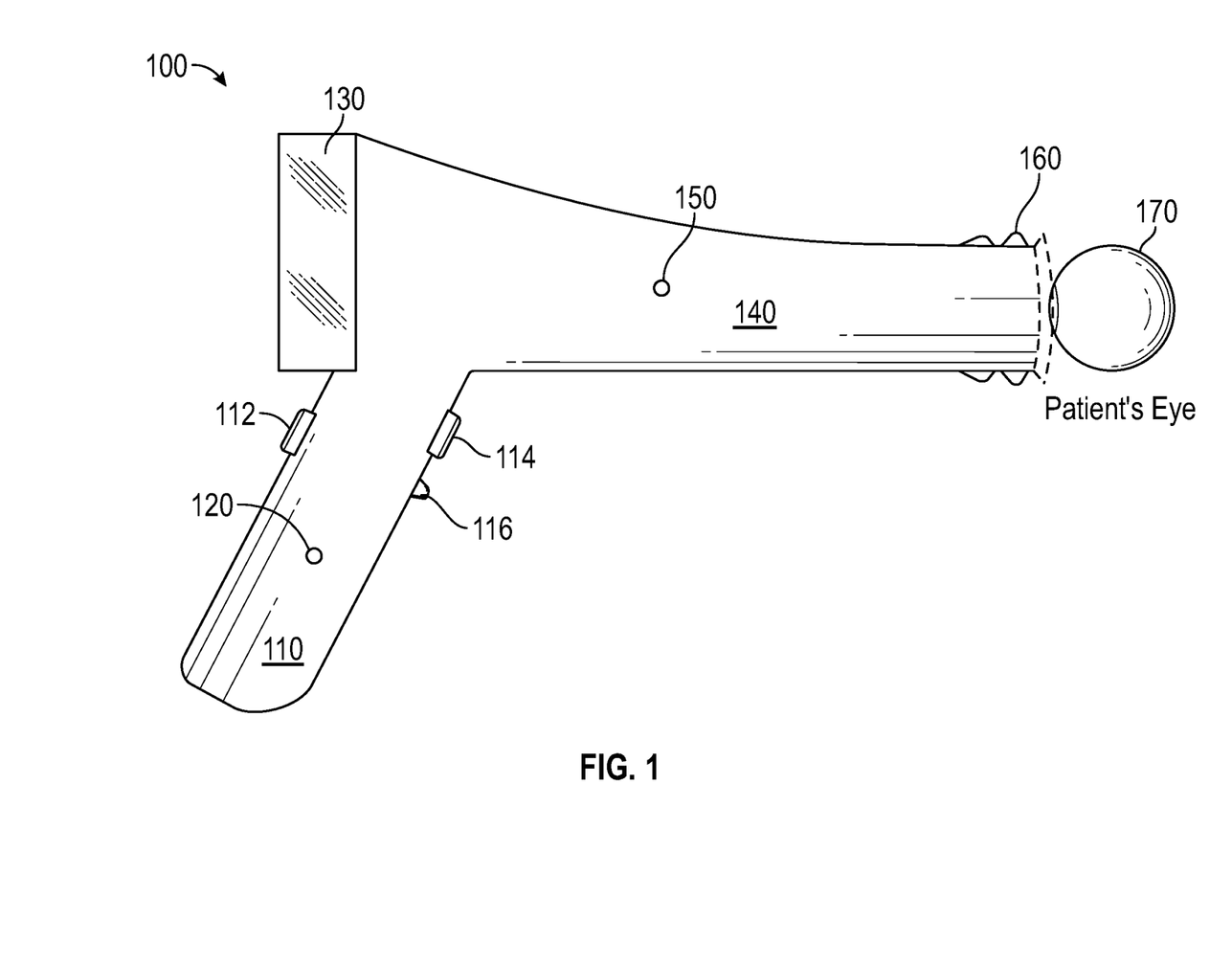
FIG. 1 illustrates a retina camera.

FIG. 1 illustrates an example retina camera 100. A housing of the retina camera 100 can include a handle 110 and a body 140 (in some cases, the body can be barrel-shaped). The handle 110 can optionally support one or more of power source, imaging optics, or electronics 120. The handle 110 can also possibly support one or more user inputs, such as a toggle control 112, a camera control 114, an optics control 116, or the like. Toggle control 112 may be used to facilitate operating a display 130 in case of a malfunction. For example, toggle control 112 can facilitate manual scrolling of the display, switching between portrait or landscape mode, or the like. Toggle control 112 can be a button. Toggle control 112 can be positioned to be accessible by a user's thumb. Camera control 114 can facilitate capturing video or an image. Camera control 114 can be a button. Camera control 114 can be positioned to be accessible by a user's index finger (such as, to simulate action of pulling a trigger) or middle finger. Optics control 116 can facilitate adjusting one or more properties of imaging optics, such as illumination adjustment, aperture adjustment, focus adjustment, zoom, etc. Optics control 116 can be a button or a scroll wheel. For example, optics control 116 can focus the imaging optics. Optics control 116 can be positioned to be accessible by a user's middle finger or index finger.

The retina camera 100 can include the display 130, which can be a liquid crystal display (LCD) or other type of display. The display 130 can be supported by the housing as illustrated in FIG. 1. For example, the display 130 can be positioned at a proximal end of the body 140. The display 130 can be one or more of a color display, high resolution display, or touch screen display. The display 130 can reproduce one or more images of the patient's eye 170. The display 130 can allow the user to control one or more imaging parameters, such as zoom, focus, or the like. The display 130 (which can be a touch screen display) can allow the user to mark whether a captured image is of sufficient quality, select a region of interest, zoom in on the image, or the like. Any of the display or buttons (such as, controls, scroll wheels, or the like) can be individually or collectively referred to as user interface. The body 140 can support one or more of the power source, imaging optics, imaging sensor, electronics 150 or any combination thereof.

A cup 160 can be positioned on (such as, removably attached to) a distal end of the body 140. The cup 160 can be made at least partially from soft and/or elastic material for contacting patient's eye orbit to facilitate examination of patient's eye 170. For example, the cup can be made of plastic, rubber, rubber-like, or foam material. Accordingly, the cup 160 may be compressible. The cup 160 can also be disposable or reusable. In some cases, the cup 160 can be sterile. The cup 160 can facilitate one or more of patient comfort, proper device placement, blocking ambient light, or the like. Some designs of the cup may also assist in establishing proper viewing distance for examination of the eye and/or pivoting for panning around the retina.

Figure 2:
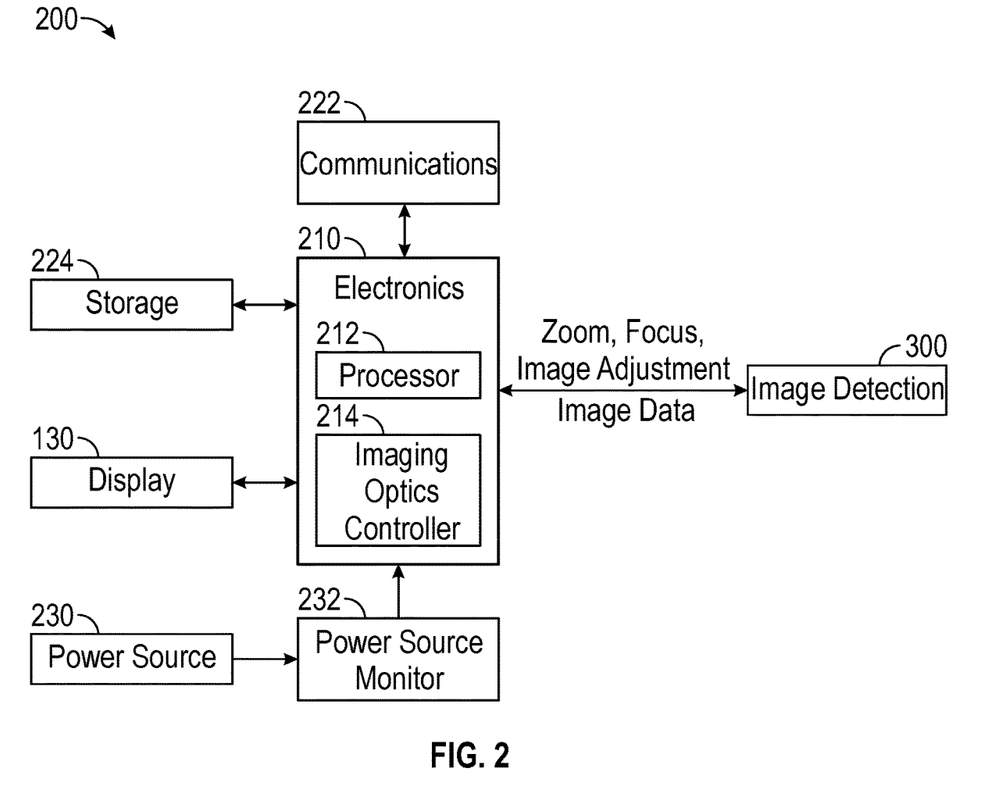
FIG. 2 schematically illustrates a system level diagram showing retina camera components of FIG. 1.

FIG. 2 illustrates a block diagram 200 of various components of the retina camera 100. Power source 230 can be configured to supply power to electronic components of the retina camera 100. Power source 230 can be supported by the handle 110, such as positioned within or attached to the handle 110 or be placed in another position on the retina camera 100. Power source 230 can include one or more batteries (which may be rechargeable). Power source 230 can receive power from a power supply (such as, a USB power supply, AC to DC power converter, or the like). Power source monitor 232 can monitor level of power (such as, one or more of voltage or current) supplied by the power source 230. Power source monitor 232 can be configured to provide one or more indications relating to the state of the power source 230, such as full capacity, low capacity, critical capacity, or the like. One or more indications (or any indications disclosed herein) can be visual, audible, tactile, or the like. Power source monitor 232 can provide one or more indications to electronics 210.

Electronics 210 can be configured to control operation of the retina camera 100. Electronics 210 can include one or more hardware circuit components (such as, one or more controllers or processors 212), which can be positioned on one or more substrates (such as, on a printed circuit board). Electronics 210 can include one or more of at least one graphics processing unit (GPU) or at least one central processing unit (CPU). Electronics 210 can be configured to operate the display 130. Storage 224 can include memory for storing data, such as image data obtained from the patient's eye 170, one or more parameters of AI detection, or the like. Any suitable type of memory can be used, including volatile or non-volatile memory, such as RAM, ROM, magnetic memory, solid-state memory, magnetoresistive random-access memory (MRAM), or the like. Electronics 210 can be configured to store and retrieve data from the storage 224.

Communications system 222 can be configured to facilitate exchange of data with another computing device (which can be local or remote). Communications system 222 can include one or more of antenna, receiver, or transmitter. In some cases, communications system 222 can support one or more wireless communications protocols, such as WiFi, Bluetooth, NFC, cellular, or the like. In some instances, the communications system can support one or more wired communications protocols, such as USB. Electronics 210 can be configured to operate communications system 222. Electronics 210 can support one or more communications protocols (such as, USB) for exchanging data with another computing device.

Electronics 210 can control an image detection system 300, which can be configured to facilitate capturing of (or capture) image data of the patient's eye 170. Electronics 210 can control one or more parameters of the image detection system 300 (for example, zoom, focus, aperture selection, image capture, provide image processing, or the like). Such control can adjust one or more properties of the image of the patient's eye 170. Electronics 210 can include an imaging optics controller 214 configured to control one or parameters of the image detection system 300. Imaging optics controller 214 can control, for example, one or more motor drivers of the image detection system 300 to drive motors (for example, to select an aperture, to select lenses that providing zoom, to move of one or more lenses to provide autofocus, to move a detector array 380 or image sensor to provide manual focus or autofocus, or the like). Control of one or more parameters of the image detection system 300 can be provided by one or more of user inputs (such as a toggle control 112, a camera control 114, an optics control 116, or the like), display 130, etc. Image detection system 300 can provide image data (which can include one or more images) to electronics 210. As disclosed herein, electronics 210 can be supported by the retina camera 100. Electronics 210 may not be configured to be attached to (such as, connected to) another computing device (such as, mobile phone or server) to perform determination of presence of a disease.

Disease Identification through Image Analysis

Electronics 210 can include one or more controllers or processors (such as, a processor 212), which can be configured to analyze one or more images to identify a disease. For example, electronics 210 can include a processing system (such as, a Jetson Nano processing system manufactured by NVIDIA or a Coral processing system manufactured by Google), a System-on-Chip (SoC), or a Field-Programmable Gate Array (FPGA) to analyze one or more images. One or more images (or photographs) or video can be captured, for example, by the user operating the camera control 114 and stored in the storage 224. One or more prompts can be output on the display 130 to guide the user (such as, "Would you like to capture video or an image?"). Additionally or alternatively, symbols and graphics may be output on the display 130 to guide the user. Image quality can be verified before or after processing the one or more images or storing the one or more images in the storage 224. If any of the one or more images is determined to be of poor quality (for instance, as compared to a quality threshold), the image may not be processed or stored, the user can be notified, or the like. Image quality can be determined based on one or more of brightness, sharpness, contrast, color accuracy, distortion, noise, dynamic range, tone reproduction, or the like.

One or more preset modes can facilitate easy and efficient capture of multiple images or video. Such one or more preset modes can automatically focus, capture, verify image quality, and store the video or image(s). For some designs the one or more preset modes can switch one or more settings (such as, switch the light source to infrared light), and repeat this cycle without user intervention. In some designs, for example, a preset mode can facilitate obtaining multiple images for subsequent analysis. Such multiple images, for example, can be taken from different angles, use different light sources, or the like. This feature can facilitate automatically collecting an image set for the patient.

The user can select a region of an image for analysis, for instance, by outlining the region on the touch screen display 130, zooming in on region of interest on the display 130, or the like. In some cases, by default the entire image may be analyzed.

One or more machine learning models (sometimes referred to as AI models) can be used to analyze one or more images or video. One or more machine learning models can be trained using training data that includes images or video of subjects having various diseases of interest, such as retina disease (retinopathy, macular degeneration, macular hole, retinal tear, retinal detachment, or the like), ocular disease (cataracts or the like), systemic disease (diabetes, hypertension, or the like), Alzheimer's disease, etc. For example, any of the machine learning models can include a convolution neural network (CNN), decision tree, support vector machine (SVM), regressions, random forest, or the like. One or more machine learning models processing such images or videos can be used for tasks such as classification, prediction, regression, clustering, reinforcement learning, dimensionality reduction. Training of one or more models can be performed using many annotated images or video (such as, thousands of images or videos, tens of thousands of images or videos, hundreds of thousands of images or videos, or the like). Training of one or more models may be performed external to the retina camera 100. Parameters of trained one or more machine learning models (such as, model weights) can be transferred to the retina camera, for example, via retina camera's wireless or wired interface (such as, USB interface). Parameters of one or more models can be stored in the storage 224 (or in another memory of electronics 210). Output of the analysis (sometimes referred to as a diagnostic report) can include one or more of determination of the presence of disease(s), severity of disease(s), character of disease(s), clinical recommendation(s) based on the likelihood of presence or absence of disease(s). A diagnostic report can be displayed on the display 130. The diagnostic report can be stored in electronic medical record (EMR) format, such as EPIC EMR, or other document format (for example, PDF). The diagnostic report can be transmitted to a computing device. In some cases, the diagnostic report but not image data can be transmitted to the computing device, which can facilitate compliance with applicable medical records regulations (such as, HIPPA, GDPR, or the like).

One or more machine learning models can determine the presence of a disease based on the output of one or more models satisfying a threshold. As described herein, images or videos can be analyzed by one or more machine learning models one at a time or in groups to determine presence of the disease. For instance, the threshold can be 90%. When images are analyzed one at a time, determination of presence of the disease can be made in response to output of one or more models satisfying 90%. When images are analyzed in a group, determination of presence of the disease can be made in response to combined outputs of one or more models analyzing the group of images satisfying 90%.

The user can provide information (or one or more tags) to increase accuracy of the analysis by one or more machine learning models. For example, the user can identify any relevant conditions, symptoms, or the like that the patient (and/or one or more patient's family members) has been diagnosed with or has experienced. Relevant conditions can include systemic disease, retinal disease, ocular disease, or the like. Relevant symptoms can include blurry vision, vision loss, headache, or the like. Symptom timing, severity, or the like can be included in the identification. The user can provide such information using one or more user interface components on the display 130, such as a drop-down list or menu. One or more tags can be stored along with one or more pertinent images in the storage 224. One or more tags can be used during analysis by one or more machine learning models during analysis and evaluation. One or more images along with one or more tags can be used as training data.

In some cases, the diagnostic report may alternatively or additionally provide information indicating increased risk of disease or condition for a physician's (such as, ophthalmologist's) consideration or indicating the presence (or absence) of disease of condition. Physician can use this information during subsequent evaluation of the patient. For example, the physician can perform further testing to determine if one or more diseases are present.

Image or video analysis, including the application of one or more machine learning models to one or more images or video, can be performed by execution of program instructions by a processor and/or by a specialized integrated circuit that implements the machine learning model in hardware.

Disclosed devices and methods can, among other things, make the process of retinal assessment comfortable, easy, efficient, and accurate. Disclosed devices and methods can be used in physician offices, clinics, emergency departments, hospitals, in telemedicine setting, or elsewhere. Unnecessary visits to a specialist healthcare provider (such as, ophthalmologist) can be avoided, and more accurate decisions to visit a specialist healthcare provider can be facilitated. In places where technological infrastructure (such as, network connectivity) is lacking, disclosed devices and methods can be used because connectivity is not needed to perform the assessment.

Interchangeable Imaging Modules

Figure 3:
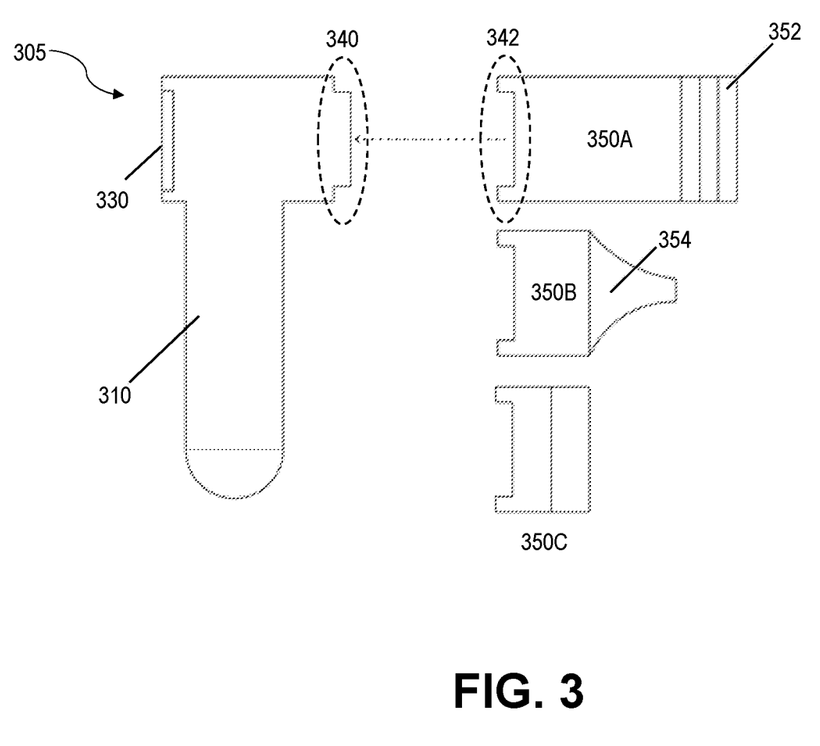
FIG. 3 illustrates a diagnostic device and several imaging modules.

FIG. 3 illustrates a diagnostic device 305 (sometimes referred to as a base unit or base system) and a plurality of interchangeable imaging modules 350A, 350B, and 350C. The imaging module 350A can be a retinal imaging module. The imaging module 350A can include an eye cup 352 (which can be similar to the cup 160). The imaging module 350B can be an ear imaging module. The imaging module 350B can include an ear specula 354 (or ear specula tip), which (similarly to the cup 160) can be used as an interface between the patient's ear and the diagnostic device. The ear specula 354 can be disposable. The imaging module 350C can be a skin imaging module.

The base system 305 can have similar features as the retina camera 100. The base system 305 can include a handle 310 (which can be similar to the handle 110) and a user interface 330 (which can be similar to the display 130). The base system 305 can include electronic components (such as, one or more controllers, communication components, or the like) as described in connection with the retina camera 100. The base system 305 can include an interface 340 configured to support the interchangeable imaging modules 350A, 350B, and 350C. As is illustrated, the interface 340 can mate with an interface 342 of the imaging module 350A. The interfaces 340 and 342 can be complementary. When the imaging module 350A is attached to the base system 305, the diagnostic device can function as a retina camera. When the imaging module 350B is attached to the base system 305, the diagnostic device can function as an otoscope. When the imaging module 350C is attached to the base system 305, the diagnostic device can function as a dermatology scope.

The interface 340 can facilitate mechanical attachment of an imaging module. The attachment can be rotational (such as, via complementary thread of the interfaces 340 and 342 or a cam-like rotational interlock). The attachment can be magnetic. For example, the interface 340 can include one or more magnets to facilitate the magnetic attachment. The one or more magnets can facilitate alignment. One or more mechanical closure mechanisms (such as, latches) can be provided to maintain secure attachment of the imaging module. The attachment may be a combination of mechanical and magnetic features. For example, a magnetic feature may draw interfaces 340 and 342 close together, which may automatically (or manually) trigger a mechanical closure mechanism.

The base system 305 can detect the attachment of an imaging module (such as, via one or more controllers). For example, an electrical signal can be generated responsive to the attachment. The electrical signal can be generated at the interface 340 (such as, via connection formed between the base system 305 and the imaging module). The base system 305 can determine the type of the imaging module attached to the base system. The determination can be made by one or more of: 1) reading a value (such as, an identifier) stored in a memory of the imaging module (such as, 0 for a retinal imaging module, 1 for an ear imaging module, or 2 for a skin imaging module); 2) receiving the value (such as, the identifier) via a communication protocol, which can be wired or wireless (such as, radio frequency identification (RFID) or near field communication (NFC)); or 3) decoding a visual marker positioned on the imaging module (such as, a quick response or QR code, colored dot, or another image pattern, which may be positioned on the exterior surface of the imaging module). In some cases, the determination can be made based on decoding the image data of a body part captured after the imaging module has been installed (such as, by detecting one or more of the anatomical features of the eye, ear, or skin in the image data).

Responsive to the determination of the type of the imaging module attached to the base system 305, one or more corresponding machine learning models configured to identify one or more diseases of the body part which the imaging module device is configured to capture images of can be loaded from a memory of the base system 305 and executed (for instance, by the one or more controllers). For example, machine learning models used to analyze images of the eye, ear, and skin may be significantly different, and each modality may require one or more specific machine learning models for detection of features, conditions, and diseases of the eye, ear, or skin. The machine learning models can be stored in the memory of the of the base system 305. When an imaging module is connected to the base system 305, the base system can detect the specific imaging module type and alter the image processing workflow in relation to the detected module type. The base system 305 can load and execute one or more particular machine learning models. One or more features of the modular architecture for the AI workflow and processing disclosed in Appendix 1 can be implemented.

For example, when the imaging module 350B for the ear is attached to the base system 305, the base system can detect that the imaging module 350B is an ear imaging module and alter the image processing workflow such that images captured are processed through the ear-specific machine learning model. In another example, when the imaging module 350B for the ear is swapped for the imaging module 350A for the eye, the base system 305 can detect the change and alter the image processing workflow such that images captured are processed through the eye-specific AI workflow. This workflow can include, for example, one or more of a diabetic retinopathy detection, glaucoma detection, or cataract detection. The base system 305 can make such workflow changes automatically responsive to a particular imaging module being attached and without the need for user input. In some instances, the user interface of the base system 305 can be automatically adjusted responsive to the attachment of a particular imaging module.

In some implementations, the machine learning models may be stored on the imaging modules (such as, in the memory), instead of being stored in the memory of the base system 305. The appropriate machine learning model(s) can be loaded and executed by the base system 305 once the imaging module has been attached or executed by one or more controllers of the imaging module.

It can be advantageous to have minimal duplication of components in the interchangeable imaging modules. To accomplish this objective, the components that serve the same function across the different imaging modules can be included in the base system 305. The base system 305 can include one or more of a user interface (such as, a display), power source, handle, electronics, buttons, triggers, imaging sensor(s), focus adjustment, or the like. The imaging modules can include components or features specific to the imaging technique or modality for which the imaging module is used. For instance, the imaging modules can include one or more of illumination specific for the body part being imaged, fixation lighting for eye-disease imaging, lenses or other optical components, contact interfaces (such as, eye cup, ear specula tips, or other attachments), baffles, or the like. In some cases, the base system can provide power to the imaging modules, which can be used to operate the illumination components and electronic components (such as, one or more controllers) of the imaging modules.

In some implementations, illumination can be included in the base system 305. In some cases, image sensor(s) can be positioned in the base system, such as proximal to the interface 340. Light gathered by the optical components of an attached imaging module can be projected on the image sensor(s) to generate video or images for processing by one or more machine learning models.

Figure 4:
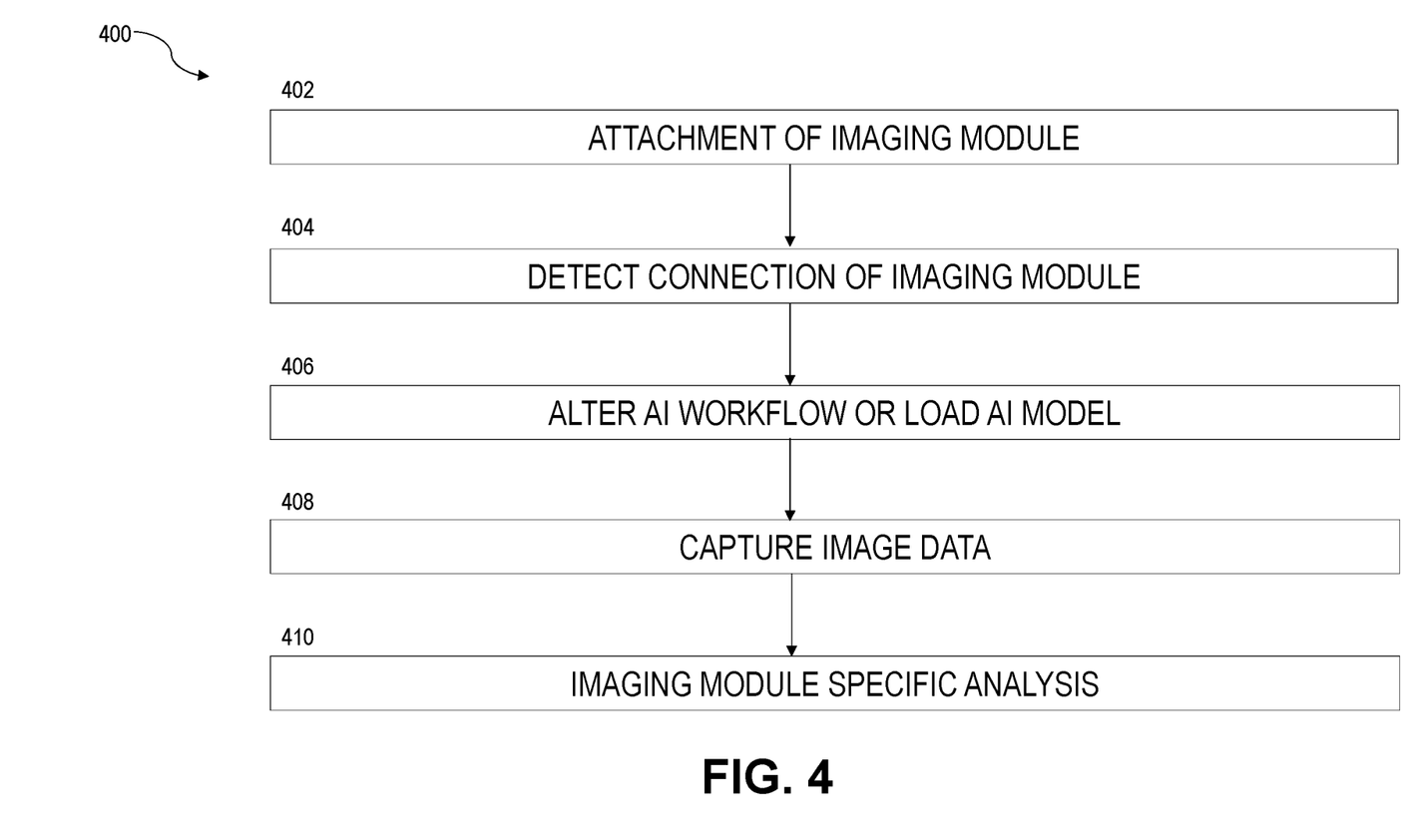
FIG. 4 illustrates a flowchart of a process for utilizing interchangeable imaging modules.

FIG. 4 illustrates a flowchart of a process 400 for utilizing interchangeable imaging modules. The process 400 can be at least partly implemented by one or more controllers of the base system 305. In block 402, an imaging module can be attached to the base system 305. In block 404, the process 400 can detect connection of an imaging module to the base system 305. In block 406, the process 400 can alter the AI workflow, which can include loading one or more particular machine learning models that correspond to the body part being imaged by the imaging module attached to the base system 305. In block 408, the process 400 can capture image data with the imaging module. In block 410, the process 400 can process the image data with the one or more machine learning modules to process the image data to determine presence (or absence) of one or more diseases.

Other Variations

Although the foregoing provides one or more examples of live image or video analysis on a retina camera, disclosed systems, devices, and methods are not limited to retina cameras, but can be extended to any diagnostics device, such as an otoscope, dermatology scope, or the like. Although the foregoing provides one or more examples of a portable medical diagnostics device, the approaches disclosed herein can be utilized by non-portable (such as, table top) diagnostics devices.

Although the foregoing provides one or more examples of live image or video analysis on-board, disclosed systems, devices, and methods are not so limited and can be utilized by cloud-based systems, particularly in situations where reliable network connectivity is available.

Example implementations are described with reference to classification of the eye tissue, but the techniques may also be applied to the classification of other tissue types. More specifically, the approach of visualizing the effects of multiple different tissue segmentations as an aid for the user to understand their effects, and hence to gain insight into the underlying explanation for the output classification, is generally applicable to many different tissue regions and types. For example, X-ray, ultrasound or MM images all produce 2D or 3D images of regions of the body, and it will be apparent that the image segmentation neural network described may be used to segment different tissue types from such images. The segmented region may then be analyzed by the classification neural network to classify the image data, for example identify one or more pathologies and/or determine one or more clinical referral decisions. Other implementations of the system may be used for screening for other pathologies in other body regions.

Any of the transmission of data described herein can be performed securely. For example, one or more of encryption, https protocol, secure VPN connection, error checking, confirmation of delivery, or the like can be utilized.

The design may vary as components may be added, removed, or modified. Depending on the embodiment, certain acts, events, or functions of any of the processes or algorithms described herein can be performed in a different sequence, can be added, merged, or left out altogether (e.g., not all described operations or events are necessary for the practice of the algorithm). Moreover, in certain embodiments, operations or events can be performed concurrently, e.g., through multi-threaded processing, interrupt processing, or multiple processors or processor cores or on other parallel architectures, rather than sequentially.

The various illustrative logical blocks, modules, routines, and algorithm steps described in connection with the embodiments disclosed herein can be implemented as electronic hardware, or combinations of electronic hardware and computer software. To clearly illustrate this interchangeability of hardware and software, various illustrative components, blocks, modules, and steps have been described above generally in terms of their functionality. Whether such functionality is implemented as hardware, or as software that runs on hardware, depends upon the particular application and design constraints imposed on the overall system. The described functionality can be implemented in varying ways for each particular application, but such implementation decisions should not be interpreted as causing a departure from the scope of the disclosure.

Moreover, the various illustrative logical blocks and modules described in connection with the embodiments disclosed herein can be implemented or performed by a machine, such as a general purpose processor device, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor device can be a microprocessor, but in the alternative, the processor device can be a controller, microcontroller, or state machine, combinations of the same, or the like. A processor device can include electronic circuitry configured to process computer-executable instructions. In another embodiment, a processor device includes an FPGA or other programmable device that performs logic operations without processing computer-executable instructions. A processor device can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor device may also include primarily analog components. For example, some or all of the signal processing algorithms described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

The elements of a method, process, routine, or algorithm described in connection with the embodiments disclosed herein can be embodied directly in hardware, in a software module executed by a processor device, or in a combination of the two. A software module can reside in RAM memory, flash memory, ROM memory, EPROM memory, EEPROM memory, registers, hard disk, a removable disk, a CD-ROM, or any other form of a non-transitory computer-readable storage medium. An example storage medium can be coupled to the processor device such that the processor device can read information from, and write information to, the storage medium. In the alternative, the storage medium can be integral to the processor device. The processor device and the storage medium can reside in an ASIC. The ASIC can reside in a user terminal. In the alternative, the processor device and the storage medium can reside as discrete components in a user terminal.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without other input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Disjunctive language such as the phrase "at least one of X, Y, Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, or within less than 0.01% of the stated amount.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations.

While the above detailed description has shown, described, and pointed out novel features as applied to various embodiments, it can be understood that various omissions, substitutions, and changes in the form and details of the devices or algorithms illustrated can be made without departing from the spirit of the disclosure. As can be recognized, certain embodiments described herein can be embodied within a form that does not provide all of the features and benefits set forth herein, as some features can be used or practiced separately from others. The scope of certain embodiments disclosed herein is indicated by the appended claims rather than by the foregoing description. All changes which come within the meaning and range of equivalency of the claims are to be embraced within their scope.

What is claimed is:

1. A medical diagnostic instrument comprising:
   a housing comprising a mounting interface configured to support a plurality of imaging devices, each of the plurality of imaging devices configured to capture an image data of a different anatomical region of a patient; and
   an electronic processing circuitry supported by the housing, the electronic processing circuitry comprising a memory and a processor, the processor configured to:
      responsive to an attachment of an imaging device of the plurality of imaging devices to the mounting interface, retrieve from the memory and execute at least one machine learning model from a plurality of machine learning models configured to identify, based on the image data, one or more diseases of the patient, the at least one machine learning model configured to identify one or more diseases of an anatomical region of the patient the image data of which the imaging device is configured to capture.

2. The instrument of claim 1, wherein the mounting interface comprises a connection configured to provide at least one of power or illumination to an imaging device attached to the mounting interface.

3. The instrument of claim 1, wherein the housing comprises an image sensor configured to capture the image data, and wherein no imaging device of the plurality of imaging devices comprises any image sensors.

4. The instrument of claim 1, wherein the processor is further configured to, responsive to the attachment of the imaging device, determine an identification of the imaging device based on at least one of: retrieving the identification from a memory of the imaging device, receiving the identification via radio frequency identification (RFID) or near field communication (NFC), determining the identification from a visual marker positioned on the imaging device, or determining the identification from the image data.

5. The instrument of claim 4, wherein the visual marker comprises a quick response (QR) code.

6. The instrument of claim 1, wherein the processor is configured to detect the attachment of the imaging device based on receiving an electrical signal generated responsive to the attachment of the imaging device.

7. The instrument of claim 1, wherein the housing further comprises a user interface at least partially supported on an exterior of the housing, and wherein the processor is further configured to configure the user interface responsive to the attachment of the imaging device.

8. The instrument of claim 7, wherein the user interface comprises a display.

9. The instrument of claim 1, wherein the mounting interface is configured to facilitate at least one of a mechanical or magnetic attachment of the imaging device.

10. The instrument of claim 1, wherein the anatomical region of the patient comprises an eye, ear, or skin of the patient.

11. The instrument of claim 1, wherein the anatomical region of the patient comprises an eye of the patient, and wherein the imaging device further comprises a cup positioned at a distal end of the imaging device, the cup configured to be an interface between the housing and the eye.

12. The instrument of claim 11, wherein the cup is disposable.

13. The instrument of claim 1, wherein the anatomical region of the patient comprises an ear of the patient, and wherein the imaging device further comprises an ear specula positioned at a distal end of the imaging device, the ear specula configured to be an interface between the housing and the ear.

14. The instrument of claim 13, wherein the ear specula is disposable.

15. The instrument of claim 1, wherein the housing comprises a body and a handle, the handle connected to the body and configured to be held by a user.

16. A method of operating a medical diagnostic instrument, the method comprising:
   by a processor of an electronic processing circuitry supported by a housing of the instrument:
   detecting an attachment of an imaging device of a plurality of imaging devices to a mounting interface positioned on the housing and configured to support the plurality of imaging devices configured to capture an image data of a different anatomical region of a patient; and responsive to detecting the attachment of the imaging device, retrieving from a memory of the electronic processing circuitry and executing at least one machine learning model from a plurality of machine learning models configured to identify, based on the image data, one or more diseases of the patient, the at least one machine learning model configured to identify one or more diseases of an anatomical region of the patient the image data of which the imaging device is configured to capture.

17. The method of claim 16, further comprising, responsive to detecting the attachment of the imaging device, determining an identification of the imaging device based on at least one of: retrieving the identification from a memory of the imaging device, receiving the identification via radio frequency identification (RFID) or near field communication (NFC), determining the identification from a visual marker positioned on the imaging device, or determining the identification from the image data.

18. The method of claim 17, wherein the visual marker comprises a quick response (QR) code.

19. The method of claim 16, wherein detecting the attachment of the imaging device is based on receiving an electrical signal generated responsive to the attachment of the imaging device.

20. The method of claim 16, wherein the different anatomical region of the patient comprises an eye, ear, or skin of the patient.

* * * * *